Aug 28, 1951 M. A. HALL Plant Pat. 1,034
VERONICA PLANT
Filed Feb. 14, 1950
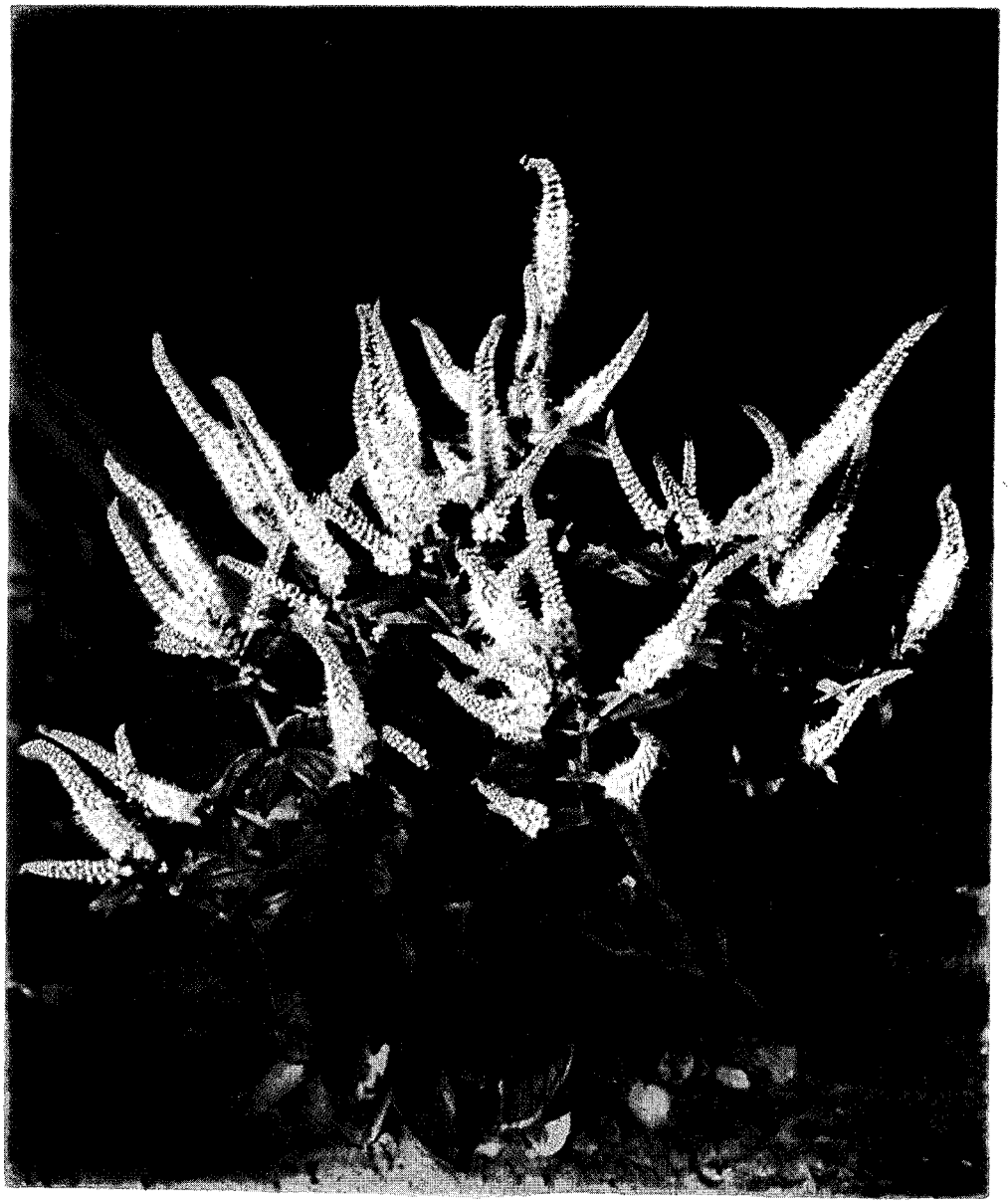
Inventor.
M. A. Hall
By: Robert Cobb
Attorneys.

Patented Aug. 28, 1951

Plant Pat. 1,034

UNITED STATES PATENT OFFICE 1,034

VERONICA PLANT

Madelene Alberta Hall, West Gravenhurst, Ontario, Canada, assignor to Jackson & Perkins Company, Newark, N. Y., a corporation of New York Application February 14, 1950, Serial No. 144,135

1 Claim. (Cl. 47—60)

The present discovery relates to a new and distinct variety of veronica plant, originating as a sport of the blue flowered form of *Veronica longifolia* Subsessilis.

The new variety was first noticed as a blue and white sport and this was later botanically clarified to a completely white clone, but otherwise having the same general characteristics of the *Veronica longifolia* Subsessilis.

This new variety is characterized primarily by its erect, compact, robust, bushy growth, averaging from 2 to 2½ feet in height, and thrives under general garden conditions, and by its great number of side branches. These characteristics, together with the clean, clear white, gracefully curved but firm spikes composed of many small florets, contrasting with the rich dark green foliage, make the plant especially effective and desirable for garden use, as well as for cut flower use. Decorators consider the spike flowers very useful for delicate high line effects, while the extremely good keeping qualities of the flowers and the wealth of bloom over a very long blooming period from the latter part of July through September, attributed to secondary blooms which follow in the axils of the leaves beneath after the main raceme has finished blooming, enhances the value of the plant for both garden and cut-flower use.

Asexual reproduction of the new variety by means of cuttings, at Newark, New York, and elsewhere, has proved that these characteristics are established and hold through succeeding propagations.

The drawing shows a typical plant of the new variety and the form and manner in which the white spike flowers are borne thereby.

The following description specifically sets forth the characteristics of the new variety, all references to color being in accordance with Ridgway's Color Standards and Nomenclature.

Observations were made in the field of Newark, New York in the morning of August 5, 1949.

Parentage: Sport of *Veronica longifolia* Subsessilis.

Classification: Botanic — *Veronica subsessilis* Alba.

*Plant*

Form: Bush—2 to 2½ feet tall, with many side branches; erect; compact; vigorous.

Foliage: Crinkled and uneven in appearance; leaves attached directly to stems.

*Size.*—2 to 4 inches long.

*Texture.*—Leathery.

*Shape.*—Oval-pointed.

*Serration.*—Single, deep.

*Ribs and veins.*—Prominent.

*Color.*—Old foliage—upper side: Dark Cress Green, Plate 31; reverse side: Light Cress Green, Plate 31. New foliage—upper side: Spinach Green, Plate 5; reverse side: Chrysolite Green, Plate 31.

Flower:

*Blooms.*—Latter part of July through September.

*Racemes.*—6 to 8 inches long, gracefully curved.

*Florets.*—Gradually open from the bottom towards the top. Size—¼ inch long and ⅜ inch diameter. Color—White, Plate 53, with throat of Rinnemann's Green, Plate 18, with an individual stamen in each floret extending about ¼ inch beyond the floret.

*Filaments and anthers.*—Color—Naples Yellow, Plate 16.

New flowering buds having the same characteristics as the center raceme, but slightly smaller in size, form in the axis of each leaf beneath the original raceme.

I claim:

A new and distinct variety of veronica plant, characterized as to novelty by the erect, compact, vigorous growth of the plant and the great number of side branches, by the rich, dark green color and the excellent form and texture of its leaves, effectively contrasting with the clear white and long, gracefully curved spike form of flowers of long-keeping quality, and by its suitability for both cut flowers and garden decorative purposes over a long blooming season in the late summer months, substantially as shown and described.

MADELENE ALBERTA HALL.

No references cited.